United States Patent [19]
Matsumoto et al.

[11] Patent Number: 4,510,332
[45] Date of Patent: Apr. 9, 1985

[54] PROCESS FOR PRODUCING 1,9-NONANEDIAL

[75] Inventors: Mitsuo Matsumoto; Noriaki Yoshimura; Masuhiko Tamura, all of Kurashiki, Japan

[73] Assignee: Kuraray Company, Ltd., Kurashiki, Japan

[21] Appl. No.: 469,699

[22] Filed: Feb. 25, 1983

[30] Foreign Application Priority Data

Mar. 12, 1982 [JP] Japan .................................. 57-39695

[51] Int. Cl.³ ............................................. C07C 45/50
[52] U.S. Cl. ................................................... 568/454
[58] Field of Search ......................................... 568/454

[56] References Cited

U.S. PATENT DOCUMENTS

| 4,215,077 | 7/1980 | Matsumoto | 568/454 |
| 4,248,802 | 2/1981 | Kuntz | 568/454 |
| 4,275,243 | 6/1981 | Saito et al. | 568/454 |
| 4,420,640 | 12/1983 | Matsumoto et al. | 568/454 |

FOREIGN PATENT DOCUMENTS 2478078  9/1981  France ................................ 568/454

Primary Examiner—Werren B. Lone
Attorney, Agent, or Firm—Oblon, Fisher, Spivak, McClelland & Maier

[57] ABSTRACT

A process for producing 1,9-nonanedial which comprises hydroformylating 7-octen-1-al with a mixture of hydrogen and carbon monoxide in an aqueous sulfolane or 1,4-butanediol solution in the presence of a rhodium complex and the sodium, potassium or lithium salt of m-(diphenylphosphino)benzenesulfonic acid, extracting 1,9-nonanedial from the reaction mixture with a primary alcohol or a mixture of a primary alcohol and a saturated aliphatic hydrocarbon, and recycling the extraction residue containing the catalyst components to the 7-octen-1-al hydroformylation step.

9 Claims, No Drawings

PROCESS FOR PRODUCING 1,9-NONANEDIAL

BACKGROUND OF THE INVENTION

1. Field of the Invention

This invention relates to a novel process for producing 1,9-nonanedial. More particularly, it relates to a process for producing 1,9-nonanedial by the hydroformylation of 7-octen-1-al which can be performed in an industrially advantageous manner.

2. Description of the Prior Art 1,9-Nonanedial is a compound which is useful as a protein- or enzyme-immobilizing agent, a disinfectant, or a starting material for the production of polyimines, azelaic acid, 1,9-nonanediol, 1,9-nonanediamine and the like. However, 1,9-nonanedial has not been produced on a commercial scale since no satisfactory advantageous method of producing the same has been found. 1,9-Nonanedial can indeed be produced by oxidizing oleic acid, which can be obtained from natural glycerides, with ozone, converting the resulting azelaic acid to an azelaic acid ester and partially (half) reducing said ester with lithium aluminum hydride or the like. However, it is difficult to selectively produce 1,9-nonanedial by such a partial reduction reaction. Moreover, the starting material and reducing agent are expensive, which makes the reaction commercially unacceptable.

SUMMARY OF THE INVENTION

Accordingly, one object of the present invention is to provide a process for producing 1,9-nonanedial in an industrially advantageous manner.

Another object of the present invention is to provide a process for producing 1,9-nonanedial in high yield from a readily available starting material.

Other objects of the present invention will become apparent as the following description proceeds.

According to the present invention, 1,9-nonanedial can be produced in high yield by (I) hydroformylating 7-octen-1-al with a mixture of hydrogen and carbon monoxide at a temperature of 40° to 110° C. in an aqueous solution of sulfolane or 1,4-butanediol in which the weight ratio of sulfolane or 1,4-butanediol to water is 15/85 to 75/25 in the presence of (a) a rhodium complex and (b) the sodium, potassium or lithium salt of m-(diphenylphosphino)benzenesulfonic acid, (II) extracting 1,9-nonanedial from the reaction mixture obtained in step (I) with a saturated aliphatic primary alcohol containing about 5 to 11 carbon atoms or a mixture of said primary alcohol and a saturated aliphatic hydrocarbon containing about 5 to 10 carbon atoms, and (III) recycling the extraction residue containing the catalyst components obtained in step (II) to the hydroformylation step (I).

DETAILED DESCRIPTION OF THE INVENTION

The 7-octen-1-al starting material for the present process can easily be prepared by a previously proposed process, by reacting butadiene with water in the presence of a palladium catalyst and isomerizing the resulting 2,7-octadien-1-ol in the presence of a catalyst comprising at least substance element from the group of copper, chromium and compounds thereof.

In the first step of the present process [I] 7-octen-1-al in hydroformylated to 1,9-nonanedial and to a branched isomer, 2-methyl-1,8-octanedial, as a byproduct. 1,9-Nonanedial and 2-methyl-1,8-octanedial are similar to each other in their chemical and physical properties and therefore it is very difficult to separate them from each other by conventional procedures. However, in the present invention, they can be separated efficiently by the method described hereinafter. 2-Methyl-1,8-octanedial is represented by the formula:

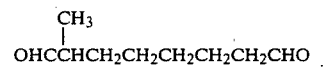

and is a novel compound not yet described in the literature.

The rhodium complex to be used in the present invention may be any of the rhodium complexes which are capable of catalyzing the hydroformylation reaction under the reaction conditions. A number of such rhodium complexes are known such as $HRh(CO)(PA_3)_3$, wherein A is an aryl group, $Rh_4(CO)_{12}$ and $Rh_6(CO)_{16}$. Rhodium complexes or compounds such as $RhCl(PA_3)_3$, $Rh(acac)_3$, $Rh(OAc)_3$, $[Rh(CO)_2(PA_3)_2]_2$, $RhCl_3.3H_2O$ and $Rh_2O_3$, wherein A is as defined above, acac is an acetylacetonato group and OAc is an acetoxy group, may also be used after activation by the conventional methods in a separate catalyst preparation vessel. The rhodium complex is generally used in the reaction in a rhodium concentration of 0.05 to 10 milligram atoms per liter of the hydroformylation reaction mixture. The sodium, potassium or lithium salt of m-(diphenylphosphino)benzenesulfonic acid is a water-soluble trisubstituted phosphine of the formula:

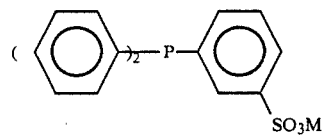

wherein M is Na, K or Li. The m-(diphenylphosphino)-benzenesulfonic acid salt is used generally in an amount of at least 10 equivalents, preferably 25 equivalents or more, per gram atom of rhodium. The m-(diphenylphosphino)benzenesulfonic acid salts may be used either singly or in a combinations of two or more thereof.

The hydroformylation of 7-octen-1-al by the present process is carried out in an aqueous solution of sulfolane or 1,4-butanediol in which the weight ratio of sulfolane or 1,4-butanediol to water is 15/85 to 75/25. The use of an aqueous solution of sulfolane is preferred from the viewpoints of the reaction results, the subsequent product separation step, chemical stability, and the like. If the weight ratio of sulfolane or, 1,4-butanediol, to water is less than 15/85, the rate of reaction is slow and the phase separability in step (II) of the process unfavorably decreases. It is also undesirable that the weight ratio exceed 75/25, because sulfolane or 1,4-butanediol and the catalyst components are transferred to an increased extent to the extract layer in step (II) of the process. It is especially desirable that the weight ratio of sulfolane or 1,4-butanediol to water range from 25/75 to 75/25.

The hydroformylation reaction is carried out at a temperature of 40° to 110° C., preferably 60° to 90° C. The mole ratio of hydrogen to carbon monoxide is generally within the range of 0.5 to 5 as the feed mixed gas composition. The reaction pressure is generally within the range of 1 to 30 atmospheres. The hydroformylation reaction can be carried out in a stirring type or bubble tower type reaction vessel in a continuous or batchwise manner. Since the solubility of 7-octen-1-al in the reaction mixture under the reaction conditions is relatively small, it is desirable to adjust the feed rate of 7-octen-1-al depending on the rate of reaction so that the reaction system can be prevented from becoming unhomogeneous. Considering such factors as the catalyst activity and the stability of the products, it is preferable that the concentration of 1,9-nonanedial in the reaction mixture be within the range of 0.5 to 3 moles per liter.

As a result of a detailed investigation it has been found that the catalyst activity can further be stabilized by providing an adequate amount of a buffer solution, typically a mixed solution containing sodium dihydrogen phosphate ($NaH_2PO_4$) and disodium hydrogen phosphate ($Na_2HPO_4$) or a mixed solution containing potassium dihydrogen phosphate ($KH_2PO_4$) and dipotassium hydrogen phosphate ($K_2HPO_4$), for instance, in the reaction zone so as to maintain the pH of the reaction mixture within the range of 5 to 7. Furthermore, it has been found that when a bidentate phosphine of the formula

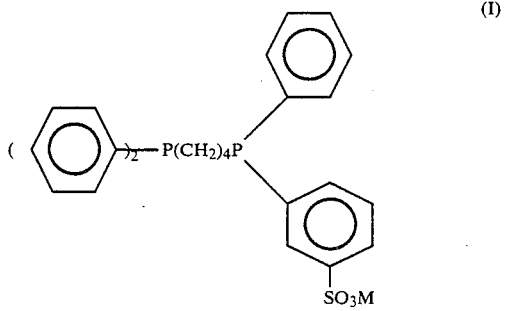

wherein M is Li, Na or K, is added to the reaction system in an amount of 0.3 to 1.5 equivalents per gram atom of rhodium, the oxidation of the above-mentioned m-(diphenylphosphino)benzenesulfonic acid salt with oxygen tends to be suppressed and the activity of the rhodium catalyst is maintained for a longer period of time.

The hydroformylation reaction mixture containing 7-octen-1-al is subjected to extraction with a saturated aliphatic primary alcohol containing about 5 to 11 carbon atoms or a mixture of said primary alcohol and a saturated aliphatic hydrocarbon containing about 5 to 10 carbon atoms. Suitable saturated aliphatic primary alcohols containing about 5 to 11 carbon atoms include, among others, n-pentanol, n-hexanol, 2-ethylhexanol, 3,5,5-trimethylhexanol, n-heptanol, n-octanol, n-nonanol, n-decanol and n-undecanol. Suitable saturated aliphatic hydrocarbon containing about 5 to 10 carbon atoms include, among others, pentane, hexane, heptane, octane, nonane and decane. The use of a mixture of said primary alcohol and said saturated aliphatic hydrocarbon can result in a diminished dissolution of sulfolane or 1,4-butanediol and catalyst components into the extract layer in comparison to when the primary alcohol is used alone. In that case, it is desirable this the ratio of the saturated aliphatic primary alcohol containing about 5 to 11 carbon atoms to the saturated aliphatic hydrocarbon containing about 5 to 10 carbon atoms (primary alcohol/saturated aliphatic hydrocarbon) be within the range of 1/20 to 20/1 by volume. When the physical properties of the extractant, such as solubility in water, boiling point and melting point, the extractability of 1,9-nonanedial, the dissolution of sulfolane or 1,4-butanediol and catalyst components, also availability of materials, prices, and other factors are taken into consideration, the use of a mixture composed of a primary alcohol selected from the group of n-pentanol, n-hexanol, n-heptanol, n-octanol and n-nonanol and a saturated aliphatic hydrocarbon selected from the group of pentane, hexane, heptane and octane is most preferred. The ratio of primary alcohol or mixture of said primary alcohol and saturated aliphatic hydrocarbon to the reaction mixture is generally within the range of 1/10 to 5/1 by volume, more preferably within the range of 1/5 to 3/1 by volume. Since the phase separability, extractability of the reaction products, dissolution of sulfolane or 1,4-butanediol and the catalyst of catalyst components are rather strongly dependent on the extraction temperature, it is industrially advantageous for the extraction temperature to be within the range of 10° to 60° C.

With regard to the extraction apparatus, such general industrial purposes type apparatus as a stirring type, RDC type or perforated plate type extraction tower may be utilized. The extraction is generally performed under an atmosphere of an inert gas such as nitrogen, helium or argon or a hydrogen-carbon monoxide mixture. The extraction transfers the reaction products and the starting material, 7-octen-1-al, to the extract (upper) layer, while the catalyst components remain in the extraction residue (lower layer). The extraction residue, if necessary after partly being subjected to a known catalyst activation treatment, is recycled to and reused in the hydroformylation step (I) (Step (III) of the process].

1,9-Nonanedial can be isolated from the extract layer obtained in step (II). The extract layer contains the reaction products, the starting material, 7-octen-1-al, and small amounts of the reaction solvent and catalyst components. Therefore, it is preferable and desirable to wash the extract layer with at least 0.01 volume of water and then isolate 1,9-nonanedial from the extract layer. Although there is no strict upper limit to the amount of water, water is generally used in a volume ratio to the extract layer of not more than 3. The sulfolane or 1,4-butanediol and catalyst components present in small amounts in the extract layer can be transferred to the aqueous layer by washing the extract layer with water, whereby the recovery of the sulfolane or 1,4-butanediol and catalyst components from the extract layer is facilitated. The aqueous solution containing sulfolane or 1,4-butanediol and catalyst components obtained by the above procedure may also be recycled to the hydroformylation step (I) after partially distilling off water from the aqueous solution. 1,9-Nonanedial can be obtained from the extract layer by a conventional distillation procedure.

According to the findings of the present invention, 1,9-nonanedial produces a crystalline precipitate of a 1,9-nonanedial dialkylhemiacetal of the formula:

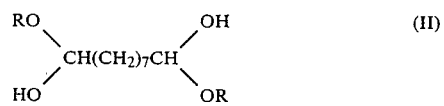

wherein R is an n-pentyl, n-hexyl, n-heptyl, n-octyl, n-nonyl or n-decyl group, by carrying out the extraction in step (II) with a primary alcohol selected from the group of n-pentanol, n-hexanol, n-heptanol, n-octanol, n-nonanol and n-decanol or a mixture of the primary alcohol and a saturated aliphatic hydrocarbon selected from the group of pentane, hexane, heptane, octane and decane, and maintaining the extract layer obtained by extraction at an adequate temperature which depends on the primary alcohol used in the extraction. Each 1,9-nonanedial dialkylhemiacetal represented by the above formula (II) is a novel compound not yet described in the literature. 2-Methyl-1,8-octanedial and the starting material, 7-octen-1-al, do not produce such a crystalline precipitate. Therefore, when this characteristic is made use of, 1,9-nonanedial especially high in purity can be obtained from the extract layer obtained in step (II). Thus, 1,9-nonanedial having a very high purity can be obtained by washing the extract layer with water, maintaining said layer at a temperature between 0° and 50° C., collecting the resulting crystalline precipitate by filtration or centrifugation or a similar procedure, washing the crystals as necessary with a small amount of water, the same primary alcohol or saturated aliphatic hydrocarbon as used in step (II), 7-octen-1-al or a mixture of these materials, and subjecting the crystals to fractional distillation. The unreacted 7-octen-1-al as well as 2-methyl-1,8-octanedial can be isolated by subjecting the mother liquor (after crystal separation) to fractional distillation. The extractant obtained by this procedure can be recycled to and reused in step (II).

1,9-Nonanedial can be converted by hydrogenation to 1,9-nonanediol which is useful as a starting material for producing polyesters and polyurethanes, for instance. In this case, the extract layer obtained in the abovementioned step (II), after washing with water, can also be subjected to the hydrogenation reaction. Furthermore, it is also possible to subject the dihemiacetal of 1,9-nonanedial with the primary alcohol used in step (II) as separated as a crystalline precipitate from the extract layer to the hydrogenation reaction.

1,9-Nonanedial can also be converted by oxidation to azelaic acid which is useful as a starting material for the production of lubricants, polyesters and plasticizers, among other uses. It can also be converted, by reaction with ammonia and hydrogen, to 1,9-nonanediamine which is useful as a starting material for the production of nylon resins and polyurethanes, for instance.

Having generally described this invention, a further understanding can be obtained by reference to certain specific examples which are provided herein for purpose of illustration only and are not intended to be limiting unless otherwise specified.

EXAMPLE 1

A one-liter stainless steel autoclave equipped with thermometer, magnetic stirrer, gas inlet and gas outlet was charged with 0.125 millimole of $Rh_4(CO)_{12}$, 50 millimoles of sodium m-(diphenylphosphino)benzenesulfonate, 250 ml of water and 250 ml of sulfolane, and then purged well with a hydrogen-carbon monoxide gaseous mixture (mole ratio 2/1). The contents were heated to 75° C. while maintaining the pressure within the autoclave at 10 atmospheres with the same gaseous mixture and the rate of flow of the effluent gas at 10 liters per hour, and then stirring was continued at a constant temperature of 75° C. for an additional 30 minutes. Thereafter, 64.3 g (500.1 millimoles) of 7-octen-1-al (purity 98%, n-octanal content 2%) was introduced into the autoclave through a metering pump continuously over an hour. After completion of the addition, stirring was continued for 1.5 hours. After the overall 2.5 hours of reaction, stirring was discontinued and the autoclave was cooled. Then, a trace amount of the reaction mixture was sampled and analyzed by gas chromatography. It was found that the amount of 7-octen-1-al was 85.3 millimoles (82.9% conversion) with the yields of 1,9-nonanedial and 2-methyl-1,8-octanedial being 348.5 millimoles and 62.2 millimoles, respectively. The reaction mixture was transferred under pressure to a three-necked 2-liter flask previously purged to a sufficient extent with a hydrogen-carbon monoxide mixture (mole ratio: 1/1) while avoiding contact of said reaction mixture with air. Then 150 ml of n-octanol and 350 ml of hexane were added, and the whole mixture was stirred in an atmosphere of the same gaseous mixture as mentioned above for 20 minutes while maintaining the internal temperature at 30° C. Upon discontinuation of the stirring, the reaction mixture immediately separated into two layers. After allowing the mixture to stand for 10 minutes, the lower (yellow) and upper (colorless) layers were analyzed by gas chromatography and it was found that 95%, 75% and 86% of 7-octen-1-al, 1,9-nonanedial and 2-methyl-1,8-octanedial, respectively, had been transferred to the upper layer. The lower layer (extraction residue) was then transferred to the autoclave while avoiding contact of said layer with air, and 10 ml of sulfolane was added. Under the same conditions as in the first run, 64.3 g of 7-octen-1-al was added continuously over an hour and thereafter stirring was continued for 1.5 hours. Analysis of the reaction mixture revealed that 87.4 millimoles of 7-octen-1-al remained unreacted and 346.8 millimoles of 1,9-nonanedial and 61.9 millimoles of 2-methyl-1,8-octanedial had been formed in the second hydroformylation reaction. The reaction mixture was subjected to the same extraction procedure under the same conditions as in the first run and the extraction residue (catalyst-containing layer) was charged into the autoclave, followed by addition of 10 ml of sulfolane. The third run of hydroformylation was carried out by the same procedure under the same conditions as in the first run. After discontinuation of reaction, the reaction mixture was analyzed and it was found that 92.4 millimoles of 7-octen-1-al remained unreacted and 342.7 millimoles of 1,9-nonanedial and 59.8 millimoles of 2-methyl-1,8-octanedial had been formed in the third hydroformylation reaction. Then, the same extraction procedure as in the first run was performed.

The extract layers obtained after the reaction and extraction steps in the above three runs were combined and washed twice with equal volumes of water and the organic layer was allowed to stand at a temperature of about 10° C. The resulting crystalline precipitate was analyzed and found to be 1,9-nonanedial dioctylhemiacetal of the formula

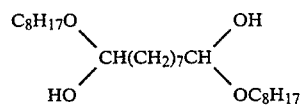

having the following physical characteristics:

Infrared absorption spectrum (KBr disk method): 3160–3400 $cm^{-1}$(broad), 2955 $cm^{-1}$, 2889 $cm^{-1}$, 2845 $cm^{-1}$, 1468 $cm^{-1}$, 1375 $cm^{-1}$, 1150 $cm^{-1}$, 1118 $cm^{-1}$, 1100 cm$^{-1}$, 1090 cm$^{-1}$, 1000 cm$^{-1}$, 958 cm$^{-1}$, 870 cm$^{-1}$.

Melting point: 42.6° C.

The crystals were collected by filtration and washed with hexane. When heated in a flask, the crystals melted easily. A conventional distillation procedure gave about 123 g of 1,9-nonanedial as the fraction boiling at 74°–75° C. under a reduced pressure of about 0.5 mmHg. Analysis by gas chromatography indicated that this fraction had a purity of not less than 98.5%. The filtrate obtained in the above procedure was subjected to reduced pressure distillation, which gave about 34 g of a mixture of 2-methyl-1,8-octanedial and 1,9-nonanedial (the content of 2-methyl-1,8-octanedial: 76%) as a fraction boiling at 73°–75° C. under a reduced pressure of about 0.5 mmHg. These products were identified by a set of spectral data.

EXAMPLE 2

The hydroformylation of 7-octen-1-al was performed in the same manner as described in Example 1 except that the reaction apparatus used in Example 1 was charged with 0.10 millimole of Rh$_6$(CO)$_{16}$, 50 millimoles of lithium m-(diphenylphosphino)benzenesulfonate, 300 ml of water and 200 ml of 1,4-butanediol. After completing the reaction, the reaction mixture was analyzed and it was found that 78.6 millimoles of 7-octen-1-al remained unchanged and the yields of 1,9-nonanedial and 2-methyl-1,8-octanedial were 345.6 millimoles and 67.1 millimoles, respectively. Then, in the same manner as in Example 1, the reaction mixture was transferred to a two-liter flask and extraction with a mixture of 100 ml of n-hexanol and 200 ml of heptane was repeated two times at a temperature of 40° C. The extract layers obtained in the two extractions were combined and washed twice with equal volumes of water and then allowed to stand at a temperature of about 10° C. White crystals precipitated. These crystals were analyzed and identified as 1,9-nonanedial dihexylhemiacetal of the formula

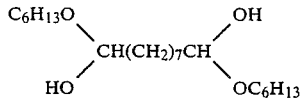

Its characteristic physical data are as follows:

Infrared absorption spectrum (KBr disk method): 3160–3500 cm$^{-1}$(broad), 2930 cm$^{-1}$, 2850 cm$^{-1}$, 1464 cm$^{-1}$, 1377 cm$^{-1}$, 1145 cm$^{-1}$, 1125 cm$^{-1}$, 1120 cm$^{-1}$, 1090 cm$^{-1}$, 960 cm$^{-1}$, 870 cm$^{-1}$.

Melting point: 31.0° C.

These crystals were collected by filtration and were subjected to distillation under the same conditions as in Example 1 to give about 41 g of 1,9-nonanedial.

Using the extraction residue obtained in the above procedure, the hydroformylation was repeated to give almost the same results as in the first run.

EXAMPLE 3

The hydroformylation of 7-octen-1-al was conducted in the same manner as described in Example 1 except that the reaction apparatus used in Example 1 was charged with 0.8 millimole of HRh(CO)[P(C$_6$H$_5$)$_3$]$_3$, 50 millimoles of potassium m-(diphenylphosphino)benzenesulfonate, 300 ml of water and 200 ml of sulfolane and that the reaction was carried out at a temperature of 80° C. while maintaining the pressure at 5 atmospheres with a hydrogen-carbon monoxide mixture in the mole ratio of 1:1. After completing the reaction, the reaction mixture was analyzed. 50.1 Millimoles of 7-octen-1-al remained unreacted and the yields of 1,9-nonanedial and 2-methyl-1,8-octanedial were 377.1 millimoles and 71.4 millimoles, respectively. The reaction mixture was then transferred to a 2-liter flask in the same manner as described in Example 1 and extracted with 300 ml of n-decanol added thereto, at a temperature of 30° C. in a nitrogen atmosphere. After allowing the mixture to stand and after phase separation, the upper layer was allowed to stand at a temperature of about 10° C. White crystals precipitated. The crystals were analyzed and identified as 1,9-nonanedial didecylhemiacetal of the formula

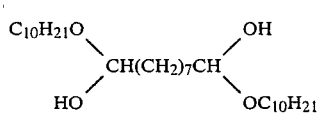

Its characteristic physical data are as follows:

Infrared absorption spectrum (KBr disk method): 3160–3400 cm$^{-1}$(broad), 2955 cm$^{-1}$, 2920 cm$^{-1}$, 2845 cm$^{-1}$, 1465 cm$^{-1}$, 1377 cm$^{-1}$, 1150 cm$^{-1}$, 1120 cm$^{-1}$, 1115 cm$^{-1}$, 955 cm$^{-1}$, 870 cm$^{-1}$.

Melting point: 48.5° C.

These crystals were collected by filtration and subjected to distillation under the same conditions as described in Example 1 to give 1,9-nonanediol.

EXAMPLE 4

A three-necked one-liter flask was charged with 0.75 millimole of HRh(CO)[P(C$_6$H$_5$)$_3$]$_3$ and sufficiently purged with a hydrogen-carbon monoxide mixture (mole ratio: 1/1). Then, 100 ml of toluene was added, the resulting mixture was stirred at 30° C. for 10 minutes, and thereafter a solution of 75 millimoles of sodium m-(diphenylphosphino)benzenesulfonate in 300 ml of water was added. The mixture was stirred for 30 minutes and then allowed to stand. The lower yellow layer (aqueous layer) was transferred to the autoclave used in Example 1 without allowing said layer to come into contact with air. The autoclave was further charged with 200 ml of sulfolane. While maintaining the pressure in the autoclave at 8 atmospheres with a hydrogen-carbon monoxide gaseous mixture (mole ratio: 3/1), 64.3 g of 7-octen-1-al was fed continuously over 1.5 hours at the effluent gas flow rate of 10 liters per hour and at the internal temperature of 75° C. After completion of the addition of gas, stirring was continued for an additional 1.5 hours. After conducting the reaction for a total of 3 hours in this manner, the reaction mixture was analyzed. There remained 41.3 millimoles of 7-octen-1-al unreacted, and the yields of 1,9-nonanedial and 2-methyl-1,8-octanedial were 422.1 millimoles and 32.0 millimoles, respectively.

Thereafter, using a mixture of 300 ml of 2-ethylhexanol and 200 ml of hexane, the same extraction procedure as described in Example 1 was carried out. After phase separation, the upper layer was washed with an equal volume of water, the hexane was distilled off, and the residue was distilled under reduced pressure to give about 57 g of a mixture of 1,9-nonanedial and 2-methyl-1,8-octanedial (1,9-nonanedial purity): 90.1%).

What we claim is:

1. A process for producing 1,9-nonanedial, which comprises the steps of:
   (I) hydroformylating 7-octen-1-al with a mixture of hydrogen and carbon monoxide in an aqueous solution of sulfolane or 1,4-butanediol in which the weight ratio of sulfolane or 1,4-butanediol to water is 15/85 to 75/25, in the presence of (a) a rhodium complex and (b) the sodium, potassium or lithium salt of m-(diphenylphosphino)-benzenesulfonic acid at a temperature of 40° C. to 110° C.;
   (II) extracting 1,9-nonanedial from the reaction mixture obtained in step (I) with a saturated aliphatic primary alcohol containing about 5 to 11 carbon atoms or a mixture of said primary alcohol and a saturated aliphatic hydrocarbon containing about 5 to 10 carbon atoms; and
   (III) recycling the extraction residue containing the catalyst components obtained in step (II) to the hydroformylation step (I).

2. The process of claim 1, wherein, in step (I), said rhodium complex is present in a rhodium concentration of 0.05 to 10 milligram atoms per liter of the reaction mixture and the sodium, potassium or lithium salt of m-(diphenylphosphino)benzenesulfonic acid is present in an amount of at least 10 equivalents per gram atom of rhodium.

3. The process of claim 1, wherein the extraction in step (II) is carried out at a temperature of 10° to 60° C. with a mixture of a primary alcohol selected from the group consisting of n-pentanol, n-hexanol, n-heptanol, n-octanol and n-nonanol and a saturated aliphatic hydrocarbon selected from the group consisting of pentane, hexane, heptane and octane.

4. The process of claim 1, wherein the extract layer obtained in step (II) is washed with water and then distilled, thereby obtaining 1,9-nonanedial.

5. The process of claim 1, wherein the extraction in step (II) is carried out at a temperature of 10° of 60° C. with a primary alcohol selected from the group consisting of n-pentanol, n-hexanol, n-heptanol, n-octanol, n-nonanol and n-decanol or a mixture of said primary alcohol and a saturated aliphatic hydrocarbon selected from the group consisting of pentane, hexane, heptane, octane, nonane and decane, followed by washing the obtained extract layer with water, maintaining the extract layer at a temperature of 0° to 50° C. to precipitate crystals of the dihemiacetal of 1,9-nonanedial with said primary alcohol, separating the crystals from said extract layer and obtaining 1,9-nonanedial by distillation.

6. The method of claim 1, wherein the hydrogen to CO mole ratio ranges from 0.5 to 5 in the feed gas to the hydroformylation step.

7. The method of claim 1, wherein said rhodium complex is $HRh(CO)(PA_3)_3$, wherein A is aryl, $Rh_4(CO)_{12}$ or $Rh_6(CO)_{16}$.

8. The method of claim 1, wherein the catalyst activity of step [I] is stabilized by buffering the reaction mixture to within the pH range of 5 to 7 with a mixture of $NaH_2PO_4$ and $Na_2HPO_4$ or mixture of $KH_2PO_4$ and $K_2HPO_4$.

9. The method of claim 1, wherein the ratio of said primary alcohol to hydrocarbon in extraction step II ranges from 1/20 to 20/1 by volume.

* * * * *

UNITED STATES PATENT AND TRADEMARK OFFICE
CERTIFICATE OF CORRECTION

PATENT NO. : 4,510,332
DATED      : April 9, 1985
INVENTOR(S): Mitsuo Matsumoto et al It is certified that error appears in the above-identified patent and that said Letters Patent is hereby corrected as shown below:

At column 1, line 37, change "description proceeds" to --is considered--;

At column 1, line 38, change "According to" to --Briefly in--;

At column 1, line 66, change "in" to --is--;

At column 2, line 24, delete "the";

At column 2, line 58, insert --,-- after "1,4-butanediol";

At column 2, line 63, insert --generally-- after "out";

At column 3, line 43, change "tends to be" to --is--;

At column 3, line 44, change "is" to --tends to be--;

At column 5, line 34, change "abovementioned" to --above-mentioned--; and

At column 8, line 31, change "1,9-nonanediol" to --1,9-nonanedial--.

Signed and Sealed this

Seventh Day of January 1986

[SEAL]

Attest:

DONALD J. QUIGG

Attesting Officer

Commissioner of Patents and Trademarks